(12) United States Patent
Templeton et al.

(10) Patent No.: US 7,145,653 B1
(45) Date of Patent: Dec. 5, 2006

(54) IN SITU PARTICLE MONITORING FOR DEFECT REDUCTION

(75) Inventors: Michael K. Templeton, Atherton, CA (US); Bharath Rangarajan, Santa Clara, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 960 days.

(21) Appl. No.: 09/591,017

(22) Filed: Jun. 9, 2000

(51) Int. Cl.
*G01N 21/00* (2006.01)

(52) U.S. Cl. ...................... 356/338; 356/343

(58) Field of Classification Search ........ 356/335–343, 356/237.1, 237.2, 237.3, 237.4, 237.5; 250/574, 250/575; 377/10, 11
See application file for complete search history.

(56) References Cited

U.S. PATENT DOCUMENTS

| | | | |
|---|---|---|---|
| 3,591,290 A * | 7/1971 | Zinner | |
| 4,637,719 A * | 1/1987 | Herman | 356/72 |
| 4,739,177 A * | 4/1988 | Borden | 250/574 |
| 4,827,143 A * | 5/1989 | Munakata et al. | 250/574 |
| 5,092,675 A * | 3/1992 | Sommer | 356/338 |
| 5,121,988 A * | 6/1992 | Blesener et al. | 356/442 |
| 5,288,333 A | 2/1994 | Tanaka et al. | 134/31 |
| 5,309,215 A * | 5/1994 | Schumann | 356/335 |
| 5,426,865 A * | 6/1995 | Ikeda et al. | 34/92 |
| 5,534,309 A | 7/1996 | Liu | 427/458 |
| 5,554,486 A | 9/1996 | Garza | 430/273.1 |
| 5,810,942 A | 9/1998 | Narayanswami et al. | 134/7 |
| 5,938,847 A * | 8/1999 | Akimoto et al. | 118/665 |
| 5,942,672 A * | 8/1999 | Harwell et al. | 73/1.07 |
| 6,034,769 A * | 3/2000 | Yufa | 356/335 |
| 6,241,827 B1 * | 6/2001 | Tanaka et al. | 134/18 |

FOREIGN PATENT DOCUMENTS

JP 411167890 * 6/1999

* cited by examiner

*Primary Examiner*—Hoa Q. Pham
(74) *Attorney, Agent, or Firm*—Amin & Turocy, LLP (57) ABSTRACT

A system and method is provided for monitoring and controlling the contaminant particle count contained in an aerosol during a photoresist coating and/or development process of a semiconductor. The monitoring system monitors the contaminate particle count present in the environment of the photoresist coating and/or development process, such as in a process chamber or a cup, enclosing the wafer during the process. The present invention employs in situ laser scattering or laser doppler anemometry techniques to detect the particle count level in the chamber or cup. A plurality of lasers and detectors can be positioned at different heights in or outside of a chamber or cup to facilitate detecting particles at different height levels. A laser could be used in conjunction with mirrors to provide a similar measurement. The particle count level can be used to compare with the defect level, so that it can be determined if a cleaner environment and/or process should be implemented.

20 Claims, 7 Drawing Sheets

IN SITU PARTICLE MONITORING FOR DEFECT REDUCTION

TECHNICAL FIELD

The present invention generally relates to semiconductor processing, and in particular to a system and method for measuring and controlling contaminates in a deposition chamber utilized in a photolithographic process.

BACKGROUND OF THE INVENTION

In the semiconductor industry, there is a continuing trend toward higher device densities. To achieve these high densities there has been and continues to be efforts toward scaling down device dimensions (e.g., at submicron levels) on semiconductor wafers. In order to accomplished such high device packing density, smaller and smaller features sizes are required. This may include the width and spacing of interconnecting lines, spacing and diameter of contact holes, and the surface geometry such as corners and edges of various features.

The requirement of small features with close spacing between adjacent features requires high resolution photolithographic processes. In general, lithography refers to processes for pattern transfer between various media. It is a technique used for integrated circuit fabrication in which a silicon slice, the wafer, is coated uniformly with a radiation-sensitive film, the resist, and an exposing source (such as optical light, x-rays, or an electron beam) illuminates selected areas of the surface through an intervening master template, the mask, for a particular pattern. The lithographic coating is generally a radiation-sensitive coating suitable for receiving a projected image of the subject pattern. Once the image is projected, it is indelibly formed in the coating. The projected image may be either a negative or a positive image of the subject pattern. Exposure of the coating through a photomask causes the image area to become either more or less soluble (depending on the coating) in a particular solvent developer. The more soluble areas are removed in the developing process to leave the pattern image in the coating as less soluble polymer.

Due to the extremely fine patterns which are exposed on the photoresist material, thickness uniformity and lack of defects in the photoresist material is a significant factor in achieving desired critical dimensions. Contaminant particles residing or introduced into the chamber where the photoresist is applied are a major cause of defects in wafers. In some cases, the contaminant particles can have thicknesses as large as the thicknesses of the wafers making the wafers virtually useless.

A typical photoresist coating process involves spinning on photoresist materal onto a wafer to form a thin film of photoresist. Some of the excess photoresist spun off from the wafer becomes an aerosol. Aerosol not removed by a cleaning system (e.g., vacuum system) may contribute to contaminating the thin photoresist film on the wafer.

In view of the above, a system/method is needed, for measuring and/or controlling contaminants particles contained in an aerosol used or formed in a lithographic process.

SUMMARY OF THE INVENTION

The present invention provides for a system and method for monitoring and controlling the contaminant particle count contained in an aerosol during a photoresist coating and/or development process of a semiconductor. The present invention accomplishes this end by monitoring the contaminate particle count present in the environment of the photoresist coating and/or development process, such as in a process chamber or a cup enclosing the wafer during the process. The present invention employs in situ laser scattering or laser doppler anemometry techniques to detect the particle count level in the chamber or cup. A plurality of lasers and detectors can be positioned at different heights in or outside a chamber or cup to facilitate detecting particles at different height levels. However, a laser could be used in conjunction with mirrors and/or beam splitter(s) to provide a similar measurement. The particle count level can be used to compare with the defect level, so that it can be determined if a cleaner environment and/or process should be implemented.

The monitoring system can also be utilized in providing a warning system to a user if the particle count exceeds a predetermined level. The warning system could also include an exhaust fan that turns on during an alarm condition to remove excessive contaminates found in the aerosols. The present invention also implements the monitoring system into a control system for controlling the contaminated particles suspended in the aerosols. A control signal can be formulated corresponding to the contaminated particle count and communicated to an exhaust flow control valve that controls an exhaust fan that is in communication with the chamber of cup. In this way, the contaminated particle count can be automatically controlled before, during and after the photoresist coating and/or development process.

One particular aspect of the invention relates to a system for monitoring particle count in a chamber. The system includes a system for sending light from the light source across the chamber; a system for receiving the light; and a system for determining particle count based upon interruptions in the light being received by the receiving system. The system may further including at least one optical waveguide to facilitate sending the light across the chamber and/or at least one optical waveguide to facilitate receiving the light and/or a beam splitter.

Another aspect of the invention relates to a system for monitoring the contaminated particle count in an aerosol found in a chamber during a photoresist coating and development process of a semiconductor. The system includes at least one laser disposed in the chamber and adapted to send a ray of light across the chamber, at least one detector disposed in the chamber and adapted to receive the ray of light and provide a signal corresponding to the intensity of the ray of light, a measuring system operably coupled to the at least one detector and adapted to receive the signal corresponding to the intensity of the ray of light and convert the signal to digital data and a processor operatively coupled to the measuring system and adapted to receive the digital data from the measuring system and analyze the digital data, wherein the difference of the intensity of the ray of light from the at least one laser to when it is received by at least one detector is proportional to the particle count in the chamber.

Another aspect of the present invention relates to a system for controlling the contaminated particle count in an aerosol found in a chamber during a photoresist coating and development process of a semiconductor. The system includes at least one laser disposed in the chamber and adapted to send a ray of light across the chamber and at least one detector disposed in the chamber adapted to receive the ray of light and provide a signal corresponding to the intensity of the ray of light. The system also includes a measuring system operably coupled to the at least one detector, which is adapted to receive the signal corresponding to the intensity of the ray of light and convert the signal to digital data. A processor is operatively coupled to the measuring system. The processor receives the digital data from the measuring system and analyzes the digital data, wherein the difference of the intensity of the ray of light from the at least one laser to when it is received by at least one detector is proportional to the particle count in the chamber. An exhaust fan is provided that is in communicative relationship with the chamber and adapted to remove contaminated particles out of the chamber. A flow control valve controls the exhaust level of the exhaust fan based on the analyzed data received from the processor.

Yet another aspect of the present invention relates to a system for monitoring the contaminated particle count in an aerosol found in a chamber during a photoresist coating and development process of a semiconductor. The system includes means for transmitting a ray of light across the chamber, means for detecting the intensity of the ray of light and providing a signal corresponding to the intensity of the ray of light, means for converting the signal to digital data and means for determining the particle count in the chamber from the digital data based on the chamber of intensity of the ray of light due to contaminated particles in the chamber.

Still another aspect of the present invention relates to a method for monitoring the contaminated particle count in an aerosol found in a chamber during a photoresist coating and development process of a semiconductor. The method includes the steps of transmitting a ray of light across the chamber, detecting the intensity of the ray of light and providing a signal corresponding to the intensity of the ray of light, converting the signal to digital data and determining the particle count in the chamber from the digital data based on the change of intensity of the ray of light due to contaminated particles in the chamber.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

DETAILED DESCRIPTION OF THE INVENTION

The present invention will now be described with reference to the drawings, wherein like reference numerals are used to refer to like refer to like elements throughout. The present invention will be described with reference to a system and method for monitoring and controlling the contaminant particle count contained in an aerosol during a photoresist coating and/or development process of a semiconductor. The following detailed description is of the best modes presently contemplated by the inventors for practicing the invention. It should be understood that the description of these preferred embodiments are merely illustrative and that they should not be taken in a limiting sense.

Figure 1:
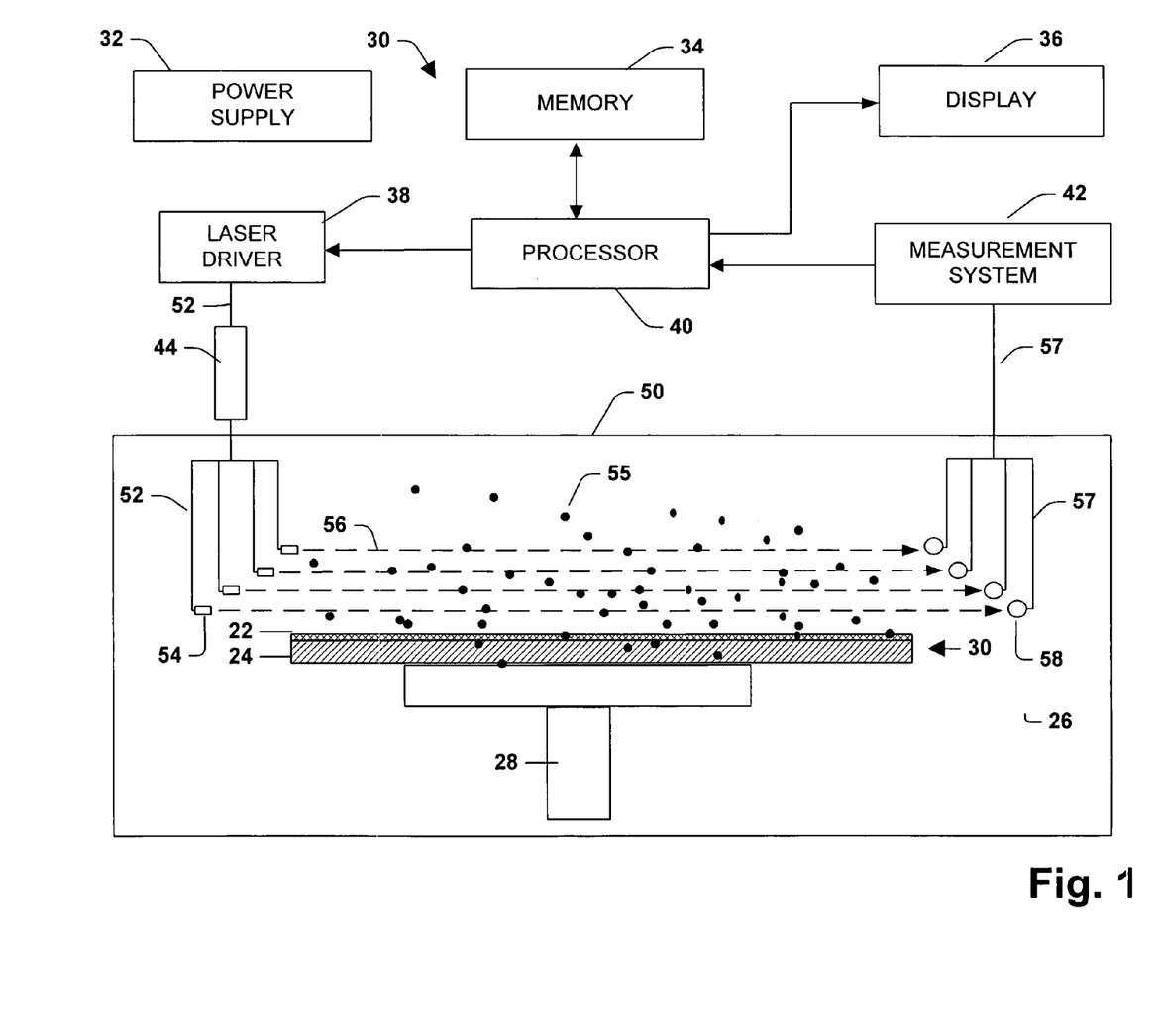
FIG. 1 is representative schematic block diagram of a monitoring system in accordance with the present invention.

Referring initially to FIG. 1, a system 30 for applying uniformly a photoresist material layer 22 on a substrate 24 to form a wafer 20 is shown. The substrate 24 is vacuum held onto a rotating chuck 26, which is spin rotated by a shaft 28 driven by a motor (not shown). The wafer 20, the rotating chuck 26 and the shaft 28 are enclosed in a chamber 50 containing a plurality of contaminated particles 55 suspended in an aerosol. The chamber 50 could be a cup adapted to hold the wafer 20, as long as the wafer 20 is isolated from the outside environment. It is to be appreciated that the present invention may be applied to other steps relating to processing of the photoresist (e.g., cooling, pre-baking, post exposure baking). Furthermore, although the present invention is primarily described within the context of monitoring and controlling contaminant particles in an aerosol, while applying a uniform layer of photoresist material to a substrate, it is to be understood that the present invention may be applied to any time period during the coating and development process. Additionally, the present invention could apply to applying uniform layers of top and bottom anti-reflective coatings, low K dielectric materials, spin-on-glass (SOG) and other spin-on materials. After the photoresist material 22 is dried, suitable photolithographic techniques may be performed to pattern the substrate 24 in a desired manner.

The system 30 further includes a particle measurement system 42. A plurality of lasers 54 (or outputs of optical waveguides transmitting laser light) within the chamber 50 are connected to a laser source 44 by fiber optic lines 52 (or other suitable optical waveguide). The laser source 44 is coupled to a laser driver 38 also by fiber optic lines 52 (or other suitable optical waveguide). It is to be appreciated that a beam splitter and/or multiple beam splitter may be employed in connection with the present invention to facilitate directing multiple beams of light in the chamber 50. The laser driver 44 is turned on and off for particle count measurements within the chamber 50 by a processor 40. The plurality of lasers 54 send rays of light 56 across the chamber 50 to a plurality of detectors 58 which are coupled to the measurement system 42 for measuring the contaminant particle count in the chamber 50. It is to be appreciated that the detectors 58 may be disposed outside of the chamber 50 and optical waveguides partly disposed within the chamber may be employed to receive the light 56 and carry the light to the detectors 58. The light 56 will be interrupted if an aerosol containing contaminant particles 55 breaks the light path 56 of the laser 54 to the detector 58, thus changing the intensity of the light 56 received by the detectors 58. Each laser 54 has a corresponding detector 58 for measuring particle counts. Each laser and detector pair are positioned at different heights in the chamber 50 to detect particles at different levels within the chamber 50. The detectors 58 are connected to the measurement system 42 by fiber optic lines 57 and provide the processor 40 with particle count information. The processor 50 analyzes the particle count information, after it is converted into digital form by the measurement system 42. The processor 40 then outputs the particle count to a display 36 in a format understandable to a user. It should be appreciated that lasers 54 and the detectors 58 may be rotatable with respect to the chamber 50 or rotate with chamber 50, if the chamber is a cup, so that particle count measurements can be performed at various points within the chamber 50 or within the cup. It should be further appreciated that four lasers 54 and four detectors 58 are shown, but any number of lasers and detectors could be employed to perform the present invention. It should be noted that a nozzle(s) for applying the photoresist material is not shown, but the optimal location of the lasers 54 and detectors 58 could be very close to the surface of wafer 20, so that lasers 54 and the detectors 58 do not interfere with the nozzle. It is to be appreciated that the system 30 will account for nozzle movement and exclude readings related thereto when determining particle count.

The measurement system 42 could utilize in-situ laser scattering or laser doppler anemometry. It should also be appreciated that the measurement system could employ polychromatic interferometer system or a monochromatic interferometer system to measure the particle count. It is to be appreciated that any suitable laser scattering, laser doppler anemometry, interferometry system and/or spectrometry system may be employed to carry out the present invention and such systems are intended to fall within the scope of the hereto appended claims. Laser scattering, laser doppler anemometry, interferometry systems and spectrometry systems are well known in the art, and therefore further discussion related thereto is omitted for sake of brevity.

The processor 40 receives the measured data from the measuring system 42 and determines the overall particle count within the chamber 50 by classical signal analysis and estimation algorithms. The processor 40 is programmed to control and operate the various components within the system 30 in order to carry out the various functions described herein. The processors or CPU 40 may be any of a plurality of processors, such as the AMD Athelon and other similar and compatible processors. The manner in which the processor 40 can be programmed to carry out the functions relating to the present invention will be readily apparent to those having ordinary skill in the art based on the description provided herein.

A memory 34 which is operatively coupled to the processor 40 is also included in the system 30 and serves to store program code executed by the processor 40 for carrying out operating functions of the system 30 as described herein. The memory 34 includes read only memory (ROM) and random access memory (RAM). The ROM contains among other code the Basic Input-Output System (BIOS) which controls the basic hardware operations of the system 30. The RAM is the main memory into which the operating system and application programs are loaded. The memory 34 also serves as a storage medium for temporarily storing information such as particle count measurements, particle count coordinate tables, laser setting information, detector sensitivity information and other data which may be employed in carrying out the present invention. For mass data storage, the memory 34 may include a hard disk drive (e.g., 10 Gigabyte hard drive).

Power supply 32 provides operating power to the system 30. Any suitable power supply (e.g., battery, line power) may be employed to carry out the present invention.

Figure 2:
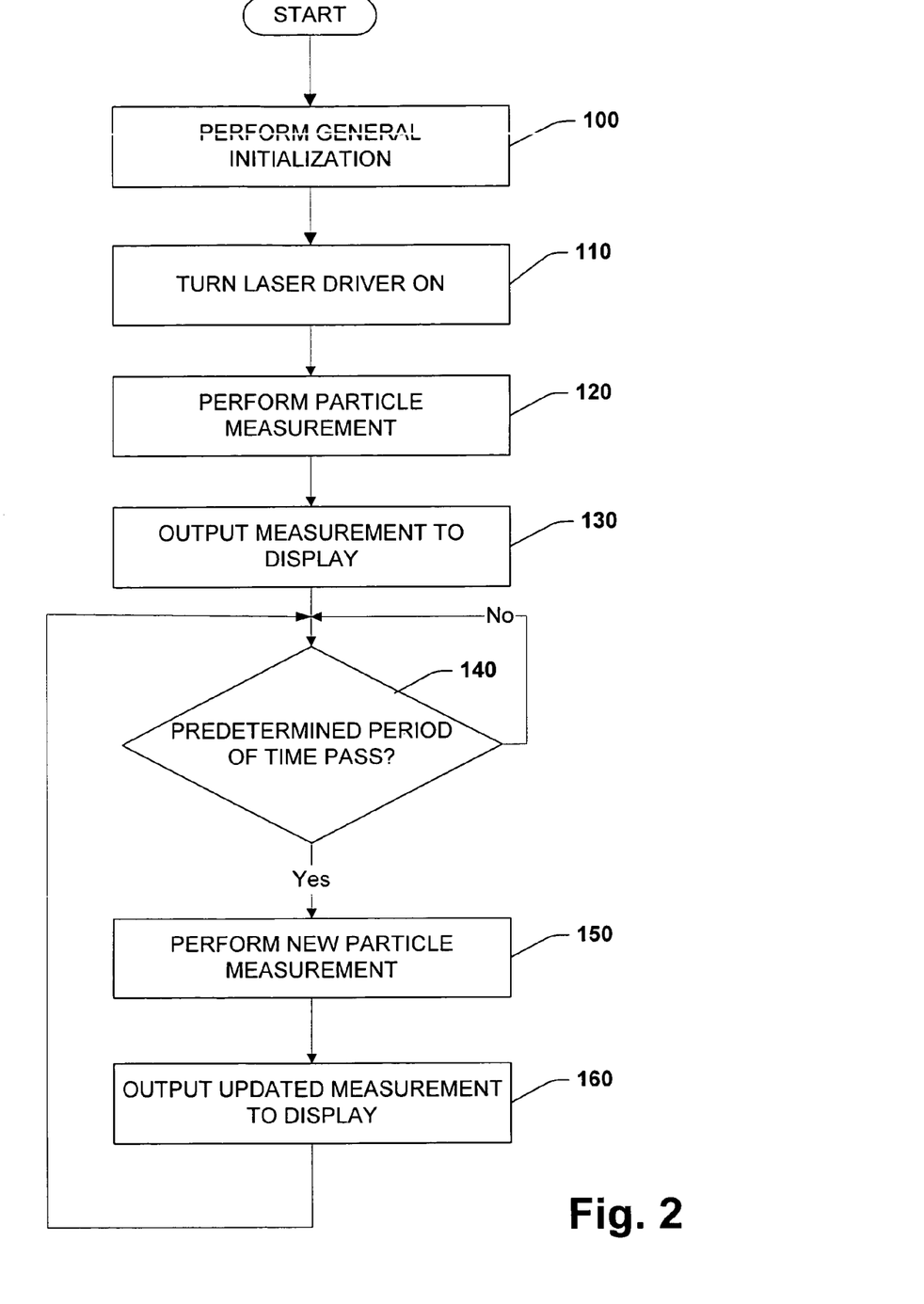
FIG. 2 illustrates one specific methodology for carrying out the monitoring system of FIG. 1 in accordance with the present invention.

FIG. 2 illustrates one particular methodology for carrying out the monitoring system of the present invention utilizing a multiple laser and detector arrangement. In step 100, power is provided to the system 30 and the processor 40 performs general initializations to the particle count monitoring system 30. In step 110, the processor 40 turns the laser driver 38 on causing lasers 54 to send beams of light 56 across the chamber 50 to detectors 58. In step 120, the measurement system 42 performs a particle count measurement and sends the data to the processor 40. In step 130, the processor 40 analyzed the measured data and outputs the data to the display 36. The processor 40 then determines if a predetermined period of time has passed in step 140. If no, the processor repeats step 140. If yes, the processor 40 advances to step 150 where a new particle measurement is performed. In step 160, the processor 40 outputs the updated measurement to the display 36 and returns to step 130. The present methodology illustrates where the system 30 performs continuous monitoring and updates to the display, and can be disabled by powering down the monitoring system. It should be noted that the processor 40 could be programmed to perform monitoring at specific periods during the coating and/or development process.

Figure 3:
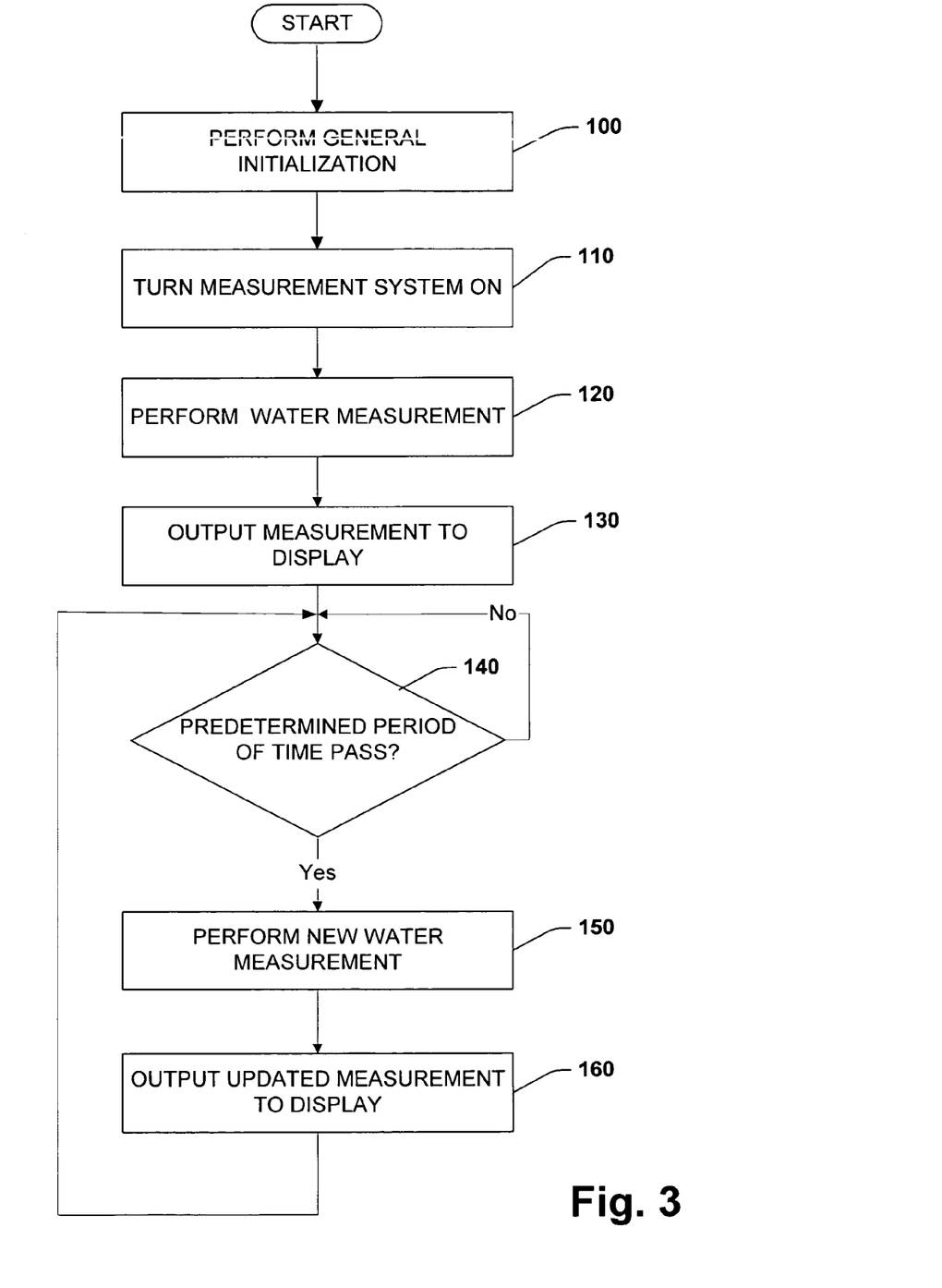
FIG. 3 is representative schematic block diagram of a warning system in accordance with the present invention.

FIG. 3 illustrates a preferred aspect of the invention where the monitoring system 30 is employed as a warning system 80. In the warning system 80, the processor 40 is coupled to an alarm 60 and an exhaust controller 65. The exhaust controller 65 controls the operation of an exhaust fan 70, which communicates with chamber 50 to remove contaminant particles 55 suspended in the chamber 50. The exhaust control and warning system 80 measures particle count similarly to the monitoring system 30, except processor 40 compares the measured value against a predetermined unacceptable particle count level. If the processor 40 detects an unacceptable particle count level, the processor 40 will transmit a control signal to the alarm 60 and the exhaust controller 65. The control signal will cause the alarm to turn on and the exhaust controller 65 will turn on the exhaust fan 70. The alarm will sound and the exhaust fan 70 will run until the chamber 50 returns to an acceptable particle count level.

Figure 4:
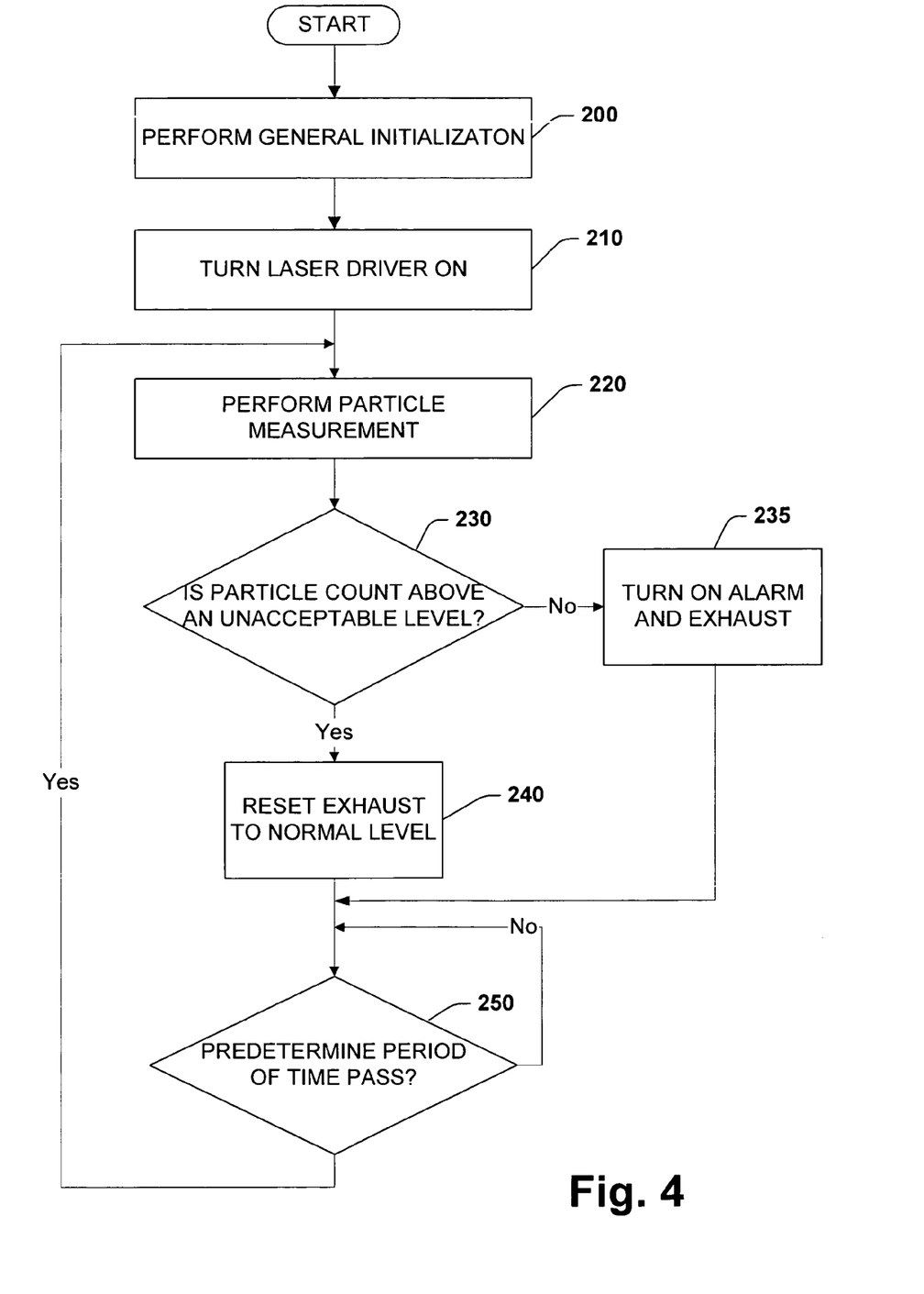
FIG. 4 illustrates one specific methodology for carrying out the warning system of FIG. 3 in accordance with the present invention.

FIG. 4 illustrates one particular methodology for carrying out the warning system of the present invention. In step 200, power is provided to the system 80 and the processor 40 performs general initializations to the particle count warning system 80. In step 210, the processor 40 turns the laser driver 38 on, causing lasers 54 to send beams of light 56 across the chamber 50 to detectors 58. In step 220, the measurement system 42 performs a particle count measurement and sends the data to the processor 40. In step 230, the processor 40 determines if the particle count in the chamber 50 is above a predetermined unacceptable level. If no, the processor 40 resets the alarm 60 and sets the exhaust fan 70 to its normal level in step 240. If yes, the processor 40 turns on the alarm 60 and the exhaust controller 65 causing the exhaust fan 70 to turn on. The processor 40 then proceeds to step 250. In step 250, the processor 40 determines if a predetermined period of time has passed. If, no the processor repeats step 250. If yes, the processor 40 returns to step 220 where another particle measurement is performed. The above example illustrates a methodology where the alarm 65 and the exhaust fan 70 remain on until the particle count returns below the predetermined unacceptable level. The user can disable the system by powering down the warning system 80. It should be noted that the processor 40 could be programmed to turn the alarm and exhaust on for a predetermined period of time, and shut down the entire system if an acceptable particle count level is never achieved.

Figure 5:
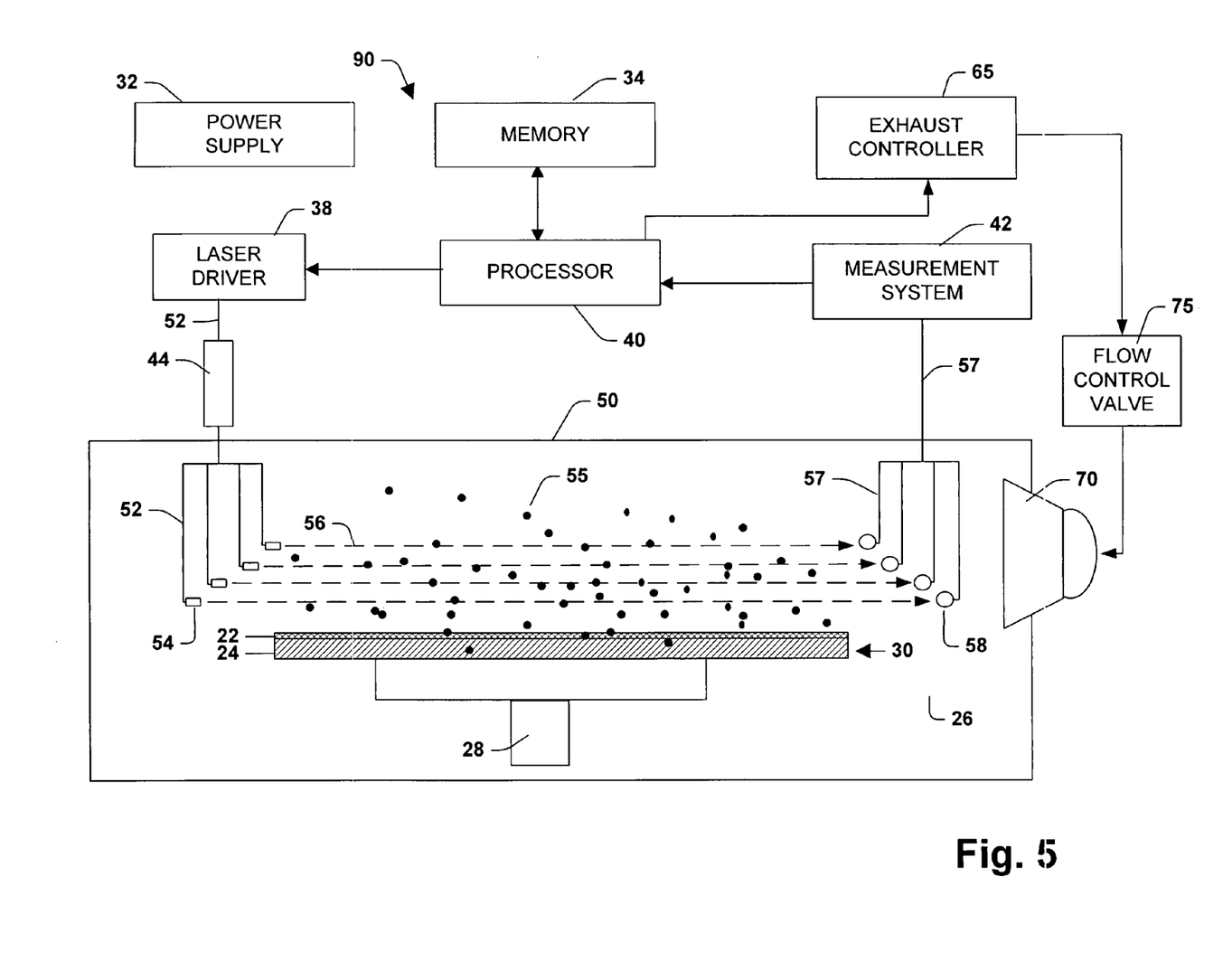
FIG. 5 is representative schematic block diagram of a control system in accordance with the present invention.
Figure 6:
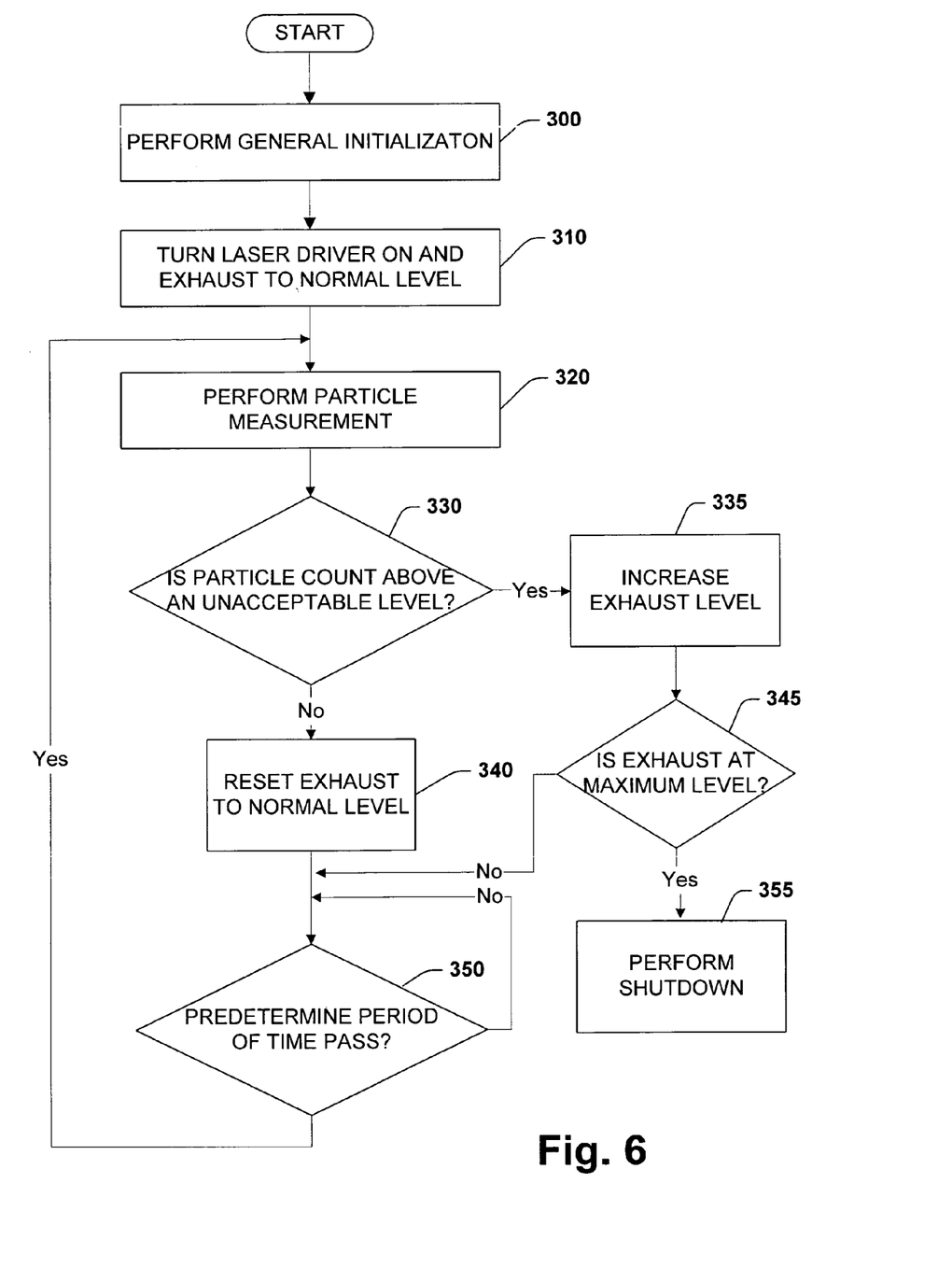
FIG. 6 illustrates one specific methodology for carrying out the control system of FIG. 5 in accordance with the present invention.
Figure 7:
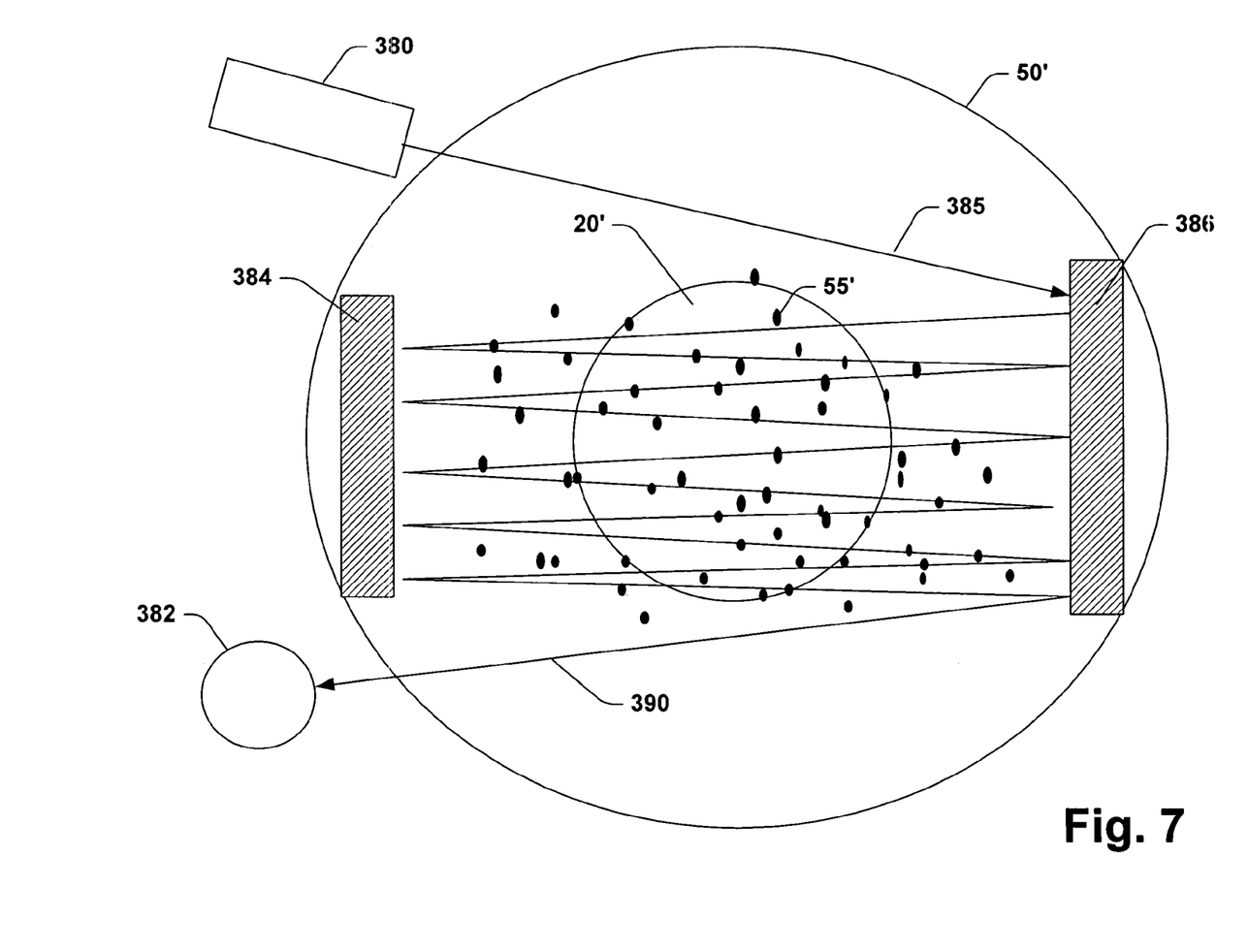
FIG. 7 is a top view of another embodiment in accordance with the present invention.

FIG. 5 illustrates a preferred aspect of the invention where the warning system 80 is employed as a control system 90. In the control system 90, the processor 40 is coupled to the exhaust controller 65, which operates a flow control valve 75. The exhaust controller 65 controls the operation of the flow control valve 75, which determines the level that the exhaust fan 70 operates. For example, the exhaust level of the fan 70, which communicates with chamber 50 to remove contaminant particles 55 suspended in the chamber 50, will increase if the amount of contaminant particles in the chamber 50 is high. The exhaust level of the exhaust fan 70 will decrease or return to a normal operation level if the contaminant particle count is low. The control system 90 ensures that the contaminant particle count level contained in the aerosol disposed in the chamber 55 is kept at a consistent level.

FIG. 6 illustrates one particular methodology for carrying out the control system of the present invention. In step 300, power is provided to the system 90 and the processor 40 performs general initializations to the particle count control system 90. In step 310, the processor 40 turns the laser driver 38 on causing lasers 54 to send beams of light 56 across the chamber 50 to detectors 58, and also informs the exhaust controller 65 to turn the exhaust fan 70 on to its normal level. In step 320, the measurement system 42 performs a particle count measurement and sends the data to the processor 40. In step 330, the processor 40 determines if the particle count in the chamber 50 is above a predetermined unacceptable level. If no, the processor 40 informs the exhaust controller 65 to reset and turn the exhaust fan 70 to its normal level in step 340. If yes, the processor 40 communicates this information to the exhaust controller 65 causing the exhaust controller 65 to adjust the flow control valve 75 and increase the level of exhaust by the exhaust fan 70. The processor 40 then proceeds to step 345 and determines if the exhaust level is at its maximum. If yes, the processor 40 performs a shutdown operation on the system 90 and preferably will send a warning to the user or operator because the system cannot achieve an acceptable particle count level. If no, the processor 40 proceeds to step 350. In step 350, the processor 40 determines if a predetermined period of time has passed. If, no the processor 40 repeats step 350. If yes, the processor 40 returns to step 320 where another particle measurement is performed.

The above example illustrates a methodology where the exhaust of the exhaust fan 70 increases until the particle count falls below the predetermined unacceptable level, and then resets the exhaust level to the normal level once the particle count is at an acceptable level. It should be noted that the processor 40 could be programmed to adjust the control valve so that the exhaust level toggles up and down based on the particle count measurement.

FIG. 7 illustrates another embodiment of the present invention. The wafer 20' is similar to the wafer 20, the chamber 50' is similar to the chamber 50, the chuck 26' is similar to the chuck 26 and the contaminated particles 55 are similar to the contaminated particles 55' illustrated in system 30 (FIG. 1), and like components include like reference numerals except that the reference numbers for like components will be followed by a prime(s) ('). Further details regarding like components is omitted to avoid redundancy.

In the embodiment shown in FIG. 7, the plurality of lasers 54 and the plurality of detectors 58 are replaced by a single laser 380 and a single detector 382. A first mirror 386 is placed on one side of chamber 50' and a second mirror 384 is placed on a side directly opposite the first mirror 386. The laser 380 transmits a beam of light 385 which reflects several times between the first mirror 386 and the second mirror 384 before it is received by the detector 382 as a beam of light 390. The reflected light travels several times through the chamber 50'. A plurality of contaminated particles 55' are suspended in an aerosol in the chamber 50'. The contaminated particles will break the light as the reflected light travels through the chamber 50' causing the intensity level detected at the detector 382 to change. The measured value can them be communicated to the processor 40 and analyzed as previously explained with reference to FIGS. 1, 3 and 5. It should be appreciated that although the embodiment of FIG. 7 shows only a single laser 282, a single detector 382 and two mirrors 384 and 386, any number of lasers, detectors and mirrors could be utilized to carry out the present invention.

What has been described above are preferred embodiments of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

What is claimed is:

1. A system that monitors and controls a contaminated particle count in a chamber during a photoresist coating and a development process, comprising:

a plurality of lasers that are positioned at different heights in the chamber with respect to a surface of a substrate, the plurality of lasers respectively transmit light across the chamber and through an aerosol that resides proximate the substrate, respective light transmissions are attenuated by contaminated particles in the aerosol;

a plurality of detectors that are positioned to receive attenuated light from respective light transmission paths and that provide respective signals that are indicative of a light intensity associated with the received attenuated light;

a measuring system that is coupled to the plurality of detectors, the measuring system converts the respective signals to digital data;

a processor that is coupled to the measuring system, the processor analyzes the digital data and generates a control signal; and an exhaust controller that receives the control signal from the processor and automatically activates an exhaust fan to remove contaminated particles from the chamber when the contaminated particle count exceeds a predetermined threshold, the exhaust controller automatically activates the exhaust fan before, during and after photoresist coating and development.

2. The system of claim 1, the measuring system applies in-situ laser scattering.

3. The system of claim 2, the measurement system applies interferometry.

4. The system of claim 1, the measuring system applies laser doppler anemometry.

5. The system of claim 1, wherein the measuring system applies spectrometry.

6. The system of claim 1, the processor outputs the analyzed data to a display.

7. The system of claim 1, the processor turns on an alarm if the contaminated particle count exceeds the predetermined threshold.

8. The system of claim 1, further comprises at least one mirror disposed in the chamber, the at least one mirror adapted to reflects the transmitted light to at least one detector.

9. The system of claim 1, the chamber is a cup.

10. A method that monitors and controls a contaminated particle count in a chamber during a photoresist coating and a development process, comprising:
- positioning a plurality of optical waveguides at various heights in the chamber with respect to a surface of a substrate;
- employing the plurality of optical waveguides to respectively transmit light through the chamber, respective light transmissions are attenuated by contaminated particles residing within respective light transmission paths;
- positioning a plurality of detectors within respective transmission paths to receive the attenuated light;
- utilizing the received light to generate respective signals that reflect a light intensity;
- digitizing the signals;
- analyzing the digitized signals to determine a contaminated particle count;
- generating a control signal based on the contaminated particle count; and
- employing the control signal to automatically remove contaminated particles from the chamber before, during and after photoresist coating and development process when the contaminated particle count exceeds a predetermined level.

11. The method of claim 10, further comprises programming a controller to turn on an alarm for a predetermined period of time when the contaminated particle count exceeds a predetermined level.

12. The method of claim 10 further comprises programming a controller to turn on an an exhaust fan for a predetermined period of time when the contaminated particle count exceeds a predetermined level.

13. The method of claim 10 further comprises programming a controller to terminate the photoresist coating and development process if the particle count continues to exceed the predetermined level after exhausting the chamber for a predetermined period of time.

14. The method of claim 10 further comprises dynamically adjusting an exhaust level in the chamber based on the contaminated particle count.

15. The method of claim 10 further comprises employing one of a beam splitter and a multiple beam splitter to direct the light transmitted by the plurality of optical waveguides to the detectors.

16. The method of claim 10 further comprises positioning the detectors outside of the chamber.

17. The method of claim 16 further comprises employing a plurality of detection optical waveguides positioned partly within the chamber to convey the received attenuated light to the detectors.

18. The method of claim 10 further comprises employing an estimation algorithm to determine the contaminated particle count.

19. The method of claim 10 further comprises determining a contaminated particle count at respective optical waveguide/detector pair heights.

20. A system that monitors and controls a contaminated particle count in a chamber during a photoresist coating and a development process of a semiconductor, comprising:
- means for transmitting light through an aerosol residing above a substrate during substrate processing within a chamber;
- means for receiving the transmitted light after the light is attenuated by contaminated particles within the aerosol;
- means for determining a contaminated particle count from the attenuated light;
- means for dynamically controlling the amount of contaminated particles in the chamber during substrate processing by cleaning the chamber when the contaminated particle count exceeds a desired level.

* * * * *

UNITED STATES PATENT AND TRADEMARK OFFICE
CERTIFICATE OF CORRECTION

PATENT NO.         : 7,145,653 B1
APPLICATION NO. : 09/591017
DATED               : December 5, 2006
INVENTOR(S)      : Michael Templeton et al.

It is certified that error appears in the above-identified patent and that said Letters Patent is hereby corrected as shown below:

Column 1, line 17: Please replace "accomplished" with --accomplish--

Column 2, line 27: Please replace "chamber of cup" with --chamber or cup--

Column 3, line 23: Please replace "chamber of intensity" with --change of intensity--

Column 4, line 6: Please replace "refer to like refer to like" with --refer to like--, deleting the repeated phrase Column 4, line 22: Please replace "contaminated particles" with --contaminant particles--

Column 5, line 41: Please replace "The processors" with --The processor--

Column 8, line 11: Please replace "value can them" with --value can then--

Signed and Sealed this

Third Day of April, 2007

JON W. DUDAS
*Director of the United States Patent and Trademark Office*